(12) United States Patent
Eldardiry et al.

(10) Patent No.: US 10,140,576 B2
(45) Date of Patent: Nov. 27, 2018

(54) COMPUTER-IMPLEMENTED SYSTEM AND METHOD FOR DETECTING ANOMALIES USING SAMPLE-BASED RULE IDENTIFICATION

(71) Applicant: Palo Alto Research Center Incorporated, Palo Alto, CA (US)

(72) Inventors: Hoda Eldardiry, San Carlos, CA (US); Sricharan Kallur Palli Kumar, Mountain View, CA (US); Daniel H. Greene, Sunnyvale, CA (US); Robert Price, Palo Alto, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 448 days.

(21) Appl. No.: 14/455,933

(22) Filed: Aug. 10, 2014

(65) Prior Publication Data

US 2016/0042287 A1   Feb. 11, 2016

(51) Int. Cl.
| | |
|---|---|
| G06F 17/00 | (2006.01) |
| G06N 5/02 | (2006.01) |
| G06F 21/00 | (2013.01) |
| G06F 21/55 | (2013.01) |
| G06Q 50/00 | (2012.01) |
| H04L 29/06 | (2006.01) |
| G06N 99/00 | (2010.01) |

(52) U.S. Cl.
CPC .............. *G06N 5/025* (2013.01); *G06F 21/00* (2013.01); *G06F 21/552* (2013.01); *G06Q 50/00* (2013.01); *H04L 63/14* (2013.01); *G06N 99/005* (2013.01)

(58) Field of Classification Search
CPC ...... G06N 5/025; G06N 99/005; H04L 63/14; G06F 21/552; G06F 21/00; G06Q 50/00
See application file for complete search history.

(56) References Cited

U.S. PATENT DOCUMENTS

| | | | |
|---|---|---|---|
| 6,782,377 B2* | 8/2004 | Agarwal | G06F 17/30707 706/21 |
| 7,627,543 B2* | 12/2009 | Lock | G06N 5/025 706/20 |
| 8,279,860 B1* | 10/2012 | Nucci | H04L 63/1416 370/356 |
| 8,284,764 B1* | 10/2012 | Nucci | H04L 41/12 370/352 |

(Continued)

OTHER PUBLICATIONS

A Classification Framework for Anomaly Detection, by Steinwart, 2005.*

(Continued)

*Primary Examiner* — Luis A Sitiriche
(74) *Attorney, Agent, or Firm* — Patrick J. S. Inouye; Leonid Kisselev (57) ABSTRACT

A computer-implemented system and method for detecting anomalies using sample-based rule identification is provided. Data for data is maintained analytics in a database. A set of anomaly rules is defined. A rare pattern in the data is statistically identified. The identified rare pattern is labeled as at least one of anomaly and non-anomaly based on verification by a domain expert. The set of anomaly rules is adjusted based on the labeled anomaly. Other anomalies in the data are detected and classified by applying the adjusted set of anomaly rules to the data.

13 Claims, 9 Drawing Sheets

(56) References Cited

U.S. PATENT DOCUMENTS

| | | | | |
|---|---|---|---|---|
| 8,468,104 | B1* | 6/2013 | Chelian | G01S 13/887 706/12 |
| 8,578,494 | B1* | 11/2013 | Engler | G06F 21/552 702/179 |
| 8,725,663 | B1* | 5/2014 | Triantaphyllou | G06N 99/005 706/12 |
| 9,262,493 | B1* | 2/2016 | Dietrich | G06F 17/30563 |
| 2003/0004902 | A1* | 1/2003 | Yamanishi | G06N 5/025 706/1 |
| 2005/0288883 | A1* | 12/2005 | Folting | G06F 17/30592 702/102 |
| 2006/0229931 | A1* | 10/2006 | Fligler | G06Q 30/02 705/7.38 |
| 2007/0195753 | A1* | 8/2007 | Judge | H04L 63/145 370/352 |
| 2007/0289013 | A1* | 12/2007 | Lim | G06F 21/552 726/22 |
| 2008/0109730 | A1* | 5/2008 | Coffman | G06Q 30/02 715/733 |
| 2008/0177813 | A1* | 7/2008 | Wang | G06K 9/00536 708/422 |
| 2010/0100521 | A1* | 4/2010 | Fujimaki | G06F 11/2257 706/47 |
| 2011/0107418 | A1* | 5/2011 | Bhagwan | G06F 21/604 726/22 |
| 2011/0119100 | A1* | 5/2011 | Ruhl | G06F 17/3089 705/7.11 |
| 2011/0185422 | A1* | 7/2011 | Khayam | H04L 63/1425 726/23 |
| 2011/0213788 | A1* | 9/2011 | Zhao | G06F 17/30702 707/751 |
| 2014/0149806 | A1* | 5/2014 | Khalastchi | G06K 9/00496 714/49 |
| 2015/0227409 | A1* | 8/2015 | Ricken | G06F 11/0709 714/47.2 |
| 2015/0341246 | A1* | 11/2015 | Boubez | H04L 43/0876 709/224 |

OTHER PUBLICATIONS

Automated Anomaly Detector Adaptation using Adaptive Threshold Tuning, by Ali, published 2009.*

An information entropy-based approach to outlier detection in rough sets, by Jiang, published 2010.*

Cemal Cagatay Bilgin and Bulent Yener. Dynamic network evolution: Models, clustering, anomaly detection. IEEE Networks, 2006.

Varun Chandola, Arindam Banerjee, and Vipin Kumar. Anomaly detection: A Survey. ACM Computing Surveys (CSUR), 41(3): 15, 2009.

Varun Chandola, Arindam Banerjee, and Vipin Kumar. Anomaly detection for discrete sequences: A survey. Knowledge and Data Engineering, IEEE Transactions on, 24(5): 823-839, 2012.

Hoda Eldardiry, Juan Liu, Ying Zhang, and Markus Fromherz. Fraud detection for healthcare. Proceedings of Knowledge, Discovery, and Data Mining 2013 workshop on Data Mining for Health Care. Aug. 2013.

Hoda Eldardiry, Kumar Sricharan, Juan Liu, John Hanley, Robert Price, Oliver Brdiczka, and Eugene Bart. Multi-source fusion for anomaly detection: using across-domain and across-time peer-group consistency checks. Journal of Wireless Mobile Networks, Ubiquitous Computing, and Dependable Applications, 5(2): 39-58, Jun. 2014.

Hoda Eldardiry and Mark Srefik. Ganging Up on Big Data. The International Conference on Collaboration Technologies and Systems, 2014.

Scott B. Wilson and Ronald Emerson. Spike detection: a review and comparison of algorithms. Clinical Neurophysiology, 113(12): 1873-1881, 2002.

* cited by examiner

COMPUTER-IMPLEMENTED SYSTEM AND METHOD FOR DETECTING ANOMALIES USING SAMPLE-BASED RULE IDENTIFICATION

FIELD

This application relates in general to data mining and, in particular, to a computer-implemented system and method for detecting anomalies using sample-based rule identification.

BACKGROUND

Data mining extracts patterns and knowledge from a large amount of data. As one of the data mining tasks, anomaly detection identifies items, events, and patterns in a data set which occurrence is considered to be rare and unusual compared with the rest of the data. Thus, anomaly detection not only enables to detect structural defects or errors in the data but also abnormal data points in the data set which is possibly a sign of abuse of the data or intrusion to a database network. Correcting the defects of errors in the data set can improve the accuracy in the data set. Further, early detection of malicious activities can provide system analysts to timely respond to such behavior and allows them to either remove the data points or make suitable changes to ensure the system operation. Anomaly detection has been expected to shed light on controlling manipulative malicious activities in the field of social welfare, credit card, transportation systems, the Internet networks, and healthcare systems.

Several different anomaly detection techniques have been proposed to identify known and unknown rare events. For example, monitoring user's behaviors and detecting two types of anomalous activities, blend-in anomalies and unusual change anomalies, for detecting malicious insiders is presented, such as described in commonly-assigned U.S. Patent Application Publication No. 2015/0235152, pending, the disclosure of which is incorporated herein by reference. Further, a combination of suspicion indicators from multiple anomaly types is presented to detect suspicious pharmacies from a large data set of pharmacy claims, as described in Eldardiry et al., Fraud Detection for Healthcare, In Proceedings of *Knowledge, Discovery, and Data Mining (KDD)* 2013 *Workshop on Data Mining for Healthcare (DMH)*, Chicago, Ill., Aug. 11, 2013, the disclosure of which is incorporated herein by reference. Moreover, for multiple domain information, an anomaly detection method for integrating multiple sources of activity data to detect insider threat is presented, as described in Eldardiry et al., Multi-Source Fusion for Anomaly Detection: Using Across-Domain and Across-Time Peer-Group Consistency Checks, *Journal of Wireless Mobile Networks, Ubiquitous Computing, and Dependable Applications*, Vol. 5(2), pp 39-58, June, 2014, the disclosure of which is incorporated herein by reference. However, the rare events do not necessarily imply that such events are malicious. For example, the rare events can be caused by other factors which arise from normal activities and may be false positive rare events. Although the existing anomaly detection techniques provide opportunities for the system analysts to review and reevaluate the rare events, casual observation by the human analysts do not contribute to the overall improvement of the anomaly detection system.

Anomaly detection techniques can be broadly categorized into two types, a rule-based method and statistical method. The rule-based method employs machine learning algorithms to identify predetermined patterns of anomalies and non-anomalies (normal) from the data set. Although the rule-based method can bring accurate and swift results of anomalies, the method is not adoptable to identify unknown anomaly patterns which are not covered by the known anomaly rules. Thus, the rule-based anomaly detection is susceptible to new forms of rare patterns which can emerge over time. To identify a broad range of rare patterns, the statistical method has been used to statistically discover rare patterns. The statistical method analyzes the data set and discovers data points which do not follow with an expected pattern or other items in the data set. Since the comparison of the data points in a specific data set is made based on an assumption that most of the data points in the data set follow a normal pattern and there is lack of domain knowledge in regard with anomalies, the data points identified as rare by the statistical method may include false positive anomalies.

Therefore, there is a need for facilitating anomaly detection methods for accurately identifying both known and unknown anomalies and reflecting domain knowledge and expertise.

SUMMARY

One embodiment provides a computer-implemented method for detecting anomalies using sample-based rule identification. Data for data analytics is maintained in a database. A rare pattern is statistically identified in the data. The identified rare pattern is identified as at least one of anomaly and non-anomaly based on verification by a domain expert. A set of anomaly rules is defined based on the labeled anomaly. Other anomalies are detected and classified in the data by applying the set of anomaly rules to the data.

Another embodiment provides a computer-implemented system and method for detecting anomalies using sample-based rule identification. Data for data analytics is maintained in a database. A set of anomaly rules is defined. A rare pattern in the data is statistically identified. The identified rare pattern is labeled as at least one of anomaly and non-anomaly based on verification by a domain expert. The set of anomaly rules is adjusted based on the labeled anomaly. The other anomalies in the data are detected and classified by applying the adjusted set of anomaly rules to the data.

Still other embodiments of the present invention will become readily apparent to those skilled in the art from the following detailed description, wherein is described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

Figure 1:
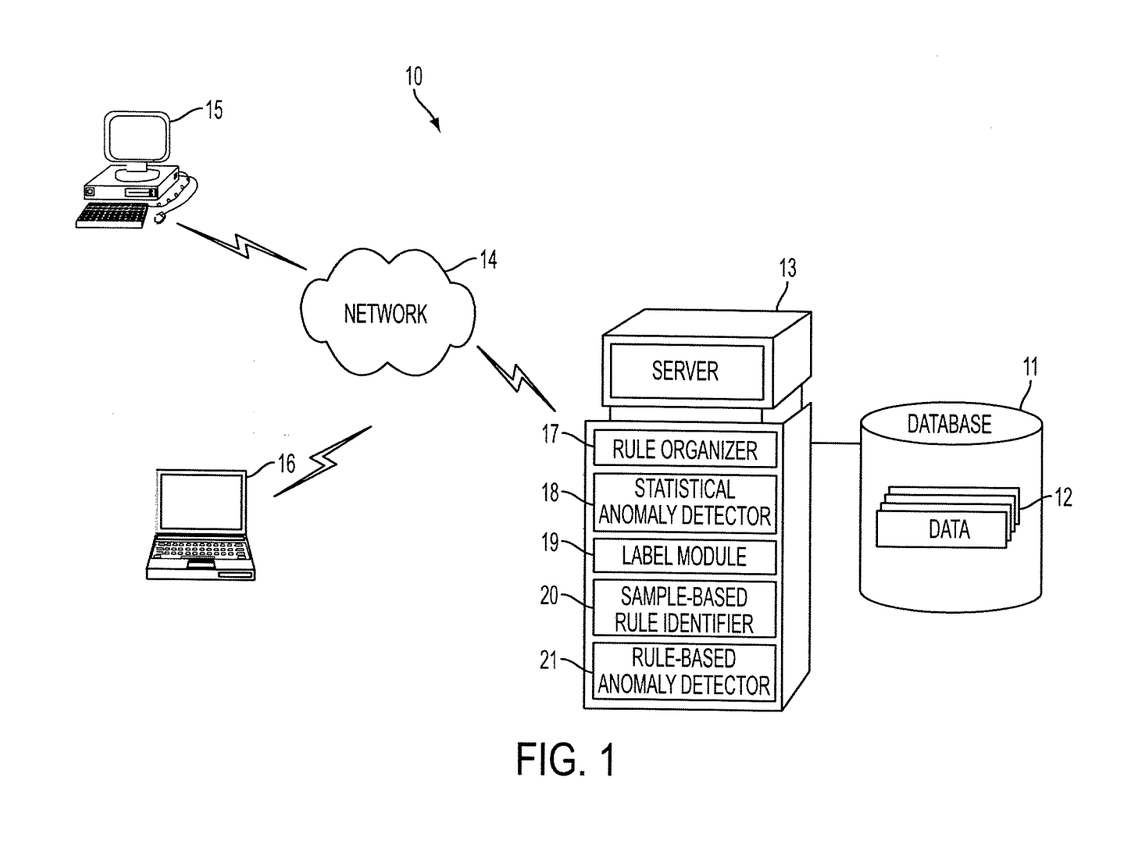
FIG. 1 is a functional block diagram showing a computer-implemented system for detecting anomalies using sample-based rule identification in accordance with one embodiment.

A feedback loop from a statistical method anomaly detection to a rule-based anomaly detection can capture more rare patterns in a data set and provide accurate identification of anomalies by incorporating domain knowledge. FIG. 1 is functional block diagram showing a computer-implemented system 10 for detecting anomalies using sample-based rule identification in accordance with one embodiment. Data analytics can be performed to analyze each data point in a data set 12 stored in a database 11. For anomaly detection, users can access to the data set 12 in the database 11 interconnected to a server 13 through a network 14 via a desktop 15 or portable computer 16. The data set 12 can include social welfare data, credit card data, transportation system data, the Internet networks, and health care data. Other data sets are possible. At a minimum, each dataset 12 should include multiple data points.

The server 13 includes a rule organizer 17, statistical anomaly detector 18, label module 19, sample-based rule identifier 20, and rule-based anomaly detector 21. The rule organizer 17 generates initial anomaly rules based on domain knowledge from system analysts and domain experts. The statistical anomaly detector 18 processes the data set 12 with a statistical anomaly detection method to identify rare patterns in the data set 12 as further discussed infra with reference to FIG. 4. Once a data point in the data set 12 is found to be rare by the statistical anomaly detection, the label module 19 assigns a label of anomaly or benign (non-anomaly), which are based on verification by domain experts. If the data point is labeled as anomaly, the initial anomaly rules generated by the domain experts are adjusted to include the data point by the sample-based rule identifier 20, as further discussed infra with reference to FIG. 5. On the other hand, if the data point statistically identified as rare is labeled as benign, then an algorithm used for the statistical method is adjusted by the statistical anomaly detector 18 not to include the data point as further discussed infra with reference to FIG. 7. In the end, all the anomaly-labeled data points are treated as anomalies. As a further process, the adjusted anomaly rules are applied by the rule-based anomaly detector 21 to the data set 12 to identify all the know patterns which are specified in the anomaly rules as further discussed infra with reference to FIG. 8.

Each computer 15, 16 includes components conventionally found in general purpose programmable computing devices, such as essential processing unit, memory, input/output ports, network interfaces, and known-volatile storage, although other components are possible. Additionally, the computers 15, 16 and server 13 can each include one or more modules for carrying out the embodiments disclosed herein. The modules can be implemented as a computer program or procedure written as a source code in a conventional programming language and is presented for execution by the central processing unit as object or byte code or written as inter-credit source code in a conventional interpreted programming language inter-credit by a language interpreter itself executed by the central processing unit as object, byte, or inter-credit code. Alternatively, the modules could also be implemented in hardware, either as intergraded circuitry or burned into read-only memory components. The various implementation of the source code and object byte codes can be held on a computer-readable storage medium, such as a floppy disk, hard drive, digital video disk (DVD), random access memory (RAM), read-only memory (ROM), and similar storage mediums. Other types of modules and module functions are possible, as well as other physical hardware components.

Figure 2:
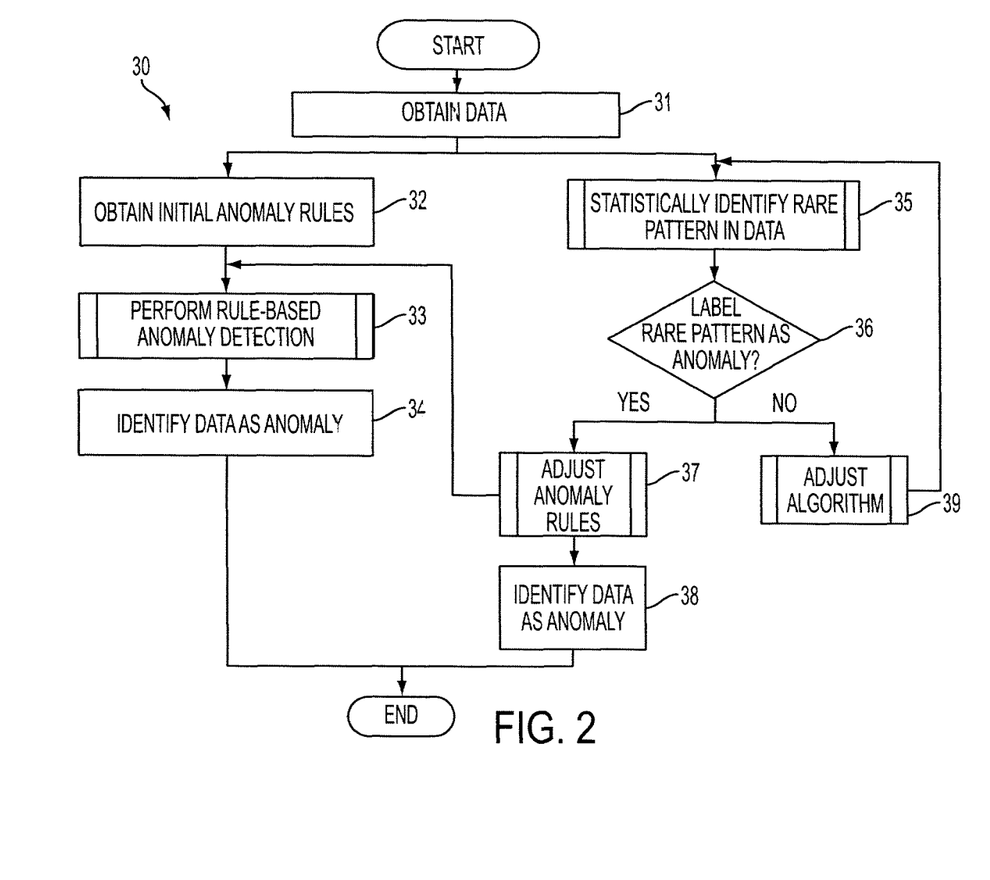
FIG. 2 is a flow diagram showing a computer-implemented method for detecting anomalies using sample-based rule identification in accordance with one embodiment.

Integrating domain expert knowledge into a combination of rule-based anomaly detection and statistical anomaly detection methods allows consideration of verification of anomalies by domain knowledge and provides a concrete accurate anomaly detection feedback system. A data set is a collection of data which is typically managed in a database. A large scale of data tends to include layers of structured data which are interrelated with other parts of data. Data analytics mathematically and statistically examines each data in the complex data structures and draws a conclusion regarding certain data or a collection of data in various different aspects. Data analytics can be performed in various fields, including enterprise management, retail management, marketing, Web analytics, credit risk analysis, and fraud analytics. In some industries, such as banking, credit card, insurance, health care, security systems, surveillance and transportation systems, discovering unusual or fraudulent data points in a data set is favored to identify malicious manipulative behavior from the data set. FIG. 2 is a flow diagram showing a computer-implemented method 30 for detecting anomalies using sample-based rule identification in accordance with one embodiment. Based on a purpose of data analytics and anomaly detection, a data set is selected (step 31).

Figure 3:
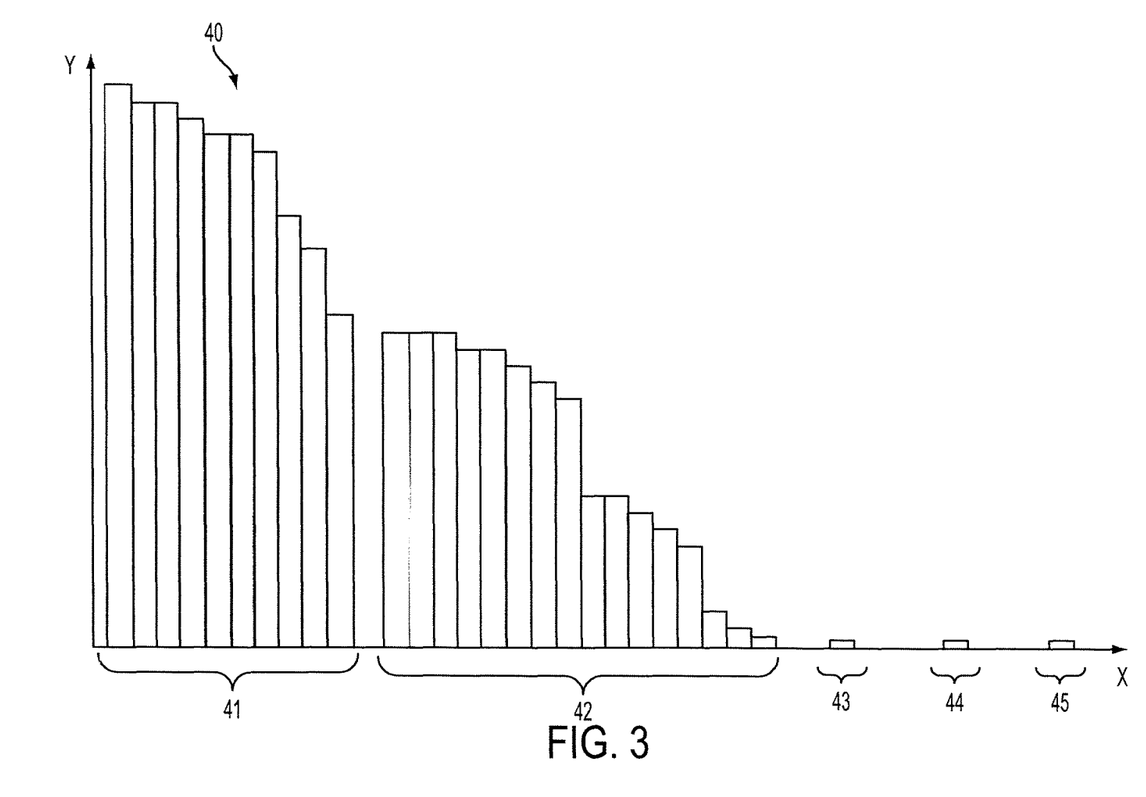
FIG. 3 is a graph depicting a simple example of anomalies in a two-dimensional data set.

Anomalies are certain data points which are considered to be outliers from other data points in a data set. Anomaly detection discloses data points in a data set which are non-conforming to the rest of the data set and notifies that the data point may convey significant information which requires immediate attention or change to maintain the system. By way of example, FIG. 3 is a graph 40 depicting a simple example of anomalies in a two-dimensional data set. The histogram 40 illustrates distribution of data. Most of data points in the histogram are observed in two regions 41, 42 and are considered to be normal data points based on a statistical analysis. On the other hand, the rest of the data points are observed in three regions, 43, 44, 45 which are far away from the two regions 41, 42, and naturally considered to be anomalies. Other examples of anomalies are possible.

One of the simplest anomaly detection techniques, a rule-based anomaly detection method, is supported by a set of known anomalies which are typically specified by domain experts. By matching the set of instances with a data set, only the anomalous data points can be identified from the data set. Referring back to FIG. 2, a set of anomaly rule specified and collected by domain experts is obtained (step 32). Then, the rule-based anomaly detection is performed to detect specific instances of know forms of manipulative data points (step 33), as further described infra with reference to FIG. 8. The specific anomalous data points are identified as anomaly (step 34).

Figure 4:
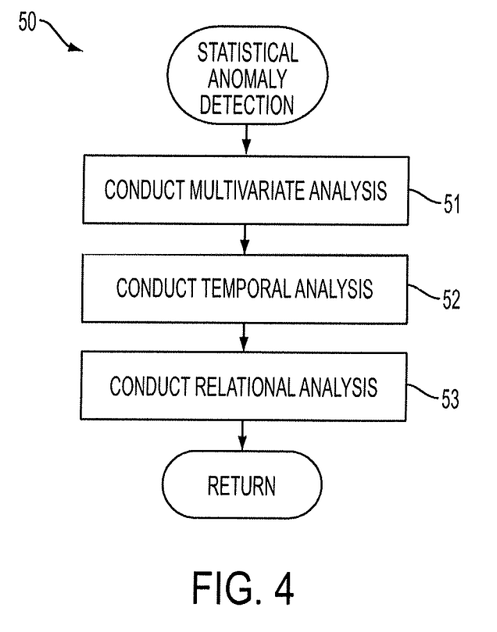
FIG. 4 is a flow diagram showing a routine for performing statistical anomaly detection to identify anomalies for use in the method of FIG. 2.

For the same data set, a statistical anomaly detection method is performed (step 35), as further described infra with reference to FIG. 4. Once rare events or patterns which are or are not captured by the rule-based anomaly detection method are extracted from the data set, those rare data points are verified by domain experts as anomaly or normal (step 36). If the rare pattern or data point is verified as anomaly, the rare data point will be added to the initial anomaly rules by being converted into a rule (step 37) and the rare data point is identified as anomaly (step 38). The conversion of the specific rare data points into an anomaly rule is further discussed infra with reference to FIGS. 6a-c. The adjusted anomaly rules are further used for the rule-based anomaly detection method for the data set to detect more instances of the particular form of anomaly. On the other hand, if the rare data point is labeled as normal by the domain experts, an algorithm used for the statistical anomaly detection method is adjusted not to include such rare data points (step 39). The adjustment of the statistical method algorithm is performed of adjusting a threshold as further discussed infra with reference to FIG. 7. The adjusted algorithm for the statistical method is used to provide more accurate identification of rare patterns. Each time a rare data point is identified by the statistical anomaly detection method, the adjustment to the initial anomaly rules and further performance of the rule-based anomaly detection method is conducted.

Although a variety of anomaly detection methods exist to identify anomalies, each of the methods tends to work only for a specific data set due to the different concept of anomaly based on each data set. The statistical anomaly detection method employs mathematical and statistical analysis of data for creating a model for normal behavior and determining if an unseen instance belongs to the model. Thus, the statistical analysis is applicable to many types of different data sets. As the statistical anomaly detection analysis, a combination of three methods will be performed. FIG. 4 is a flow diagram showing a routine 50 for performing statistical anomaly detection to identify anomalies for use in the method of FIG. 2. First, the multivariate statistical method is performed (step 51). Multivariate statistical methods provide identifying a group of specific data whose behaviors are rare compared to the rest of the population. This identification can possibly indicate some forms of self-centered manipulative behaviors. The statistical multivariate anomaly detection methods for detecting anomalies have been established, such as described in Chandola et al., Anomaly Detection: A Survey, *ACM Computing Surveys (CSUR)*, Vol. 41(3) Article No. 15, pp 33-39 (2009), the disclosures of which are incorporated herein by reference. Then, a temporal statistical method is performed (step 52). The temporal statistical method statistically captures rare trends in specific data with regard to time. For examples, abnormal amounts of slot trades at a particular time instance can be detected using spike detection. Finding anomalies from a discrete sequence of data, such as a finite unordered alphabet, has been established, such as described in Chandola et al., Anomaly Detection for Discrete Sequences: A Survey, *IEEE Transactions on Knowledge and Data Engineering*, Vol. 25, No. 5, pp 1-16 (2012). Finally, a statistical relational mining approach is performed (step 53). The statistical relational mining approach focuses on describing correlation in certain behaviors between groups. Such a relational mining approach has been established, such as described in Schoubridge et al., Detection of abnormal change in a time series of graphs, *Journal of Interconnection Networks*, Vol. 3, pp 85-101 (2002) and Bilgin and Yener, Dynamic Network Evolution: Models, Clustering, Anomaly Detection, *IEEE Networks* (2006), the disclosures of which are incorporated herein by reference.

Figure 5:
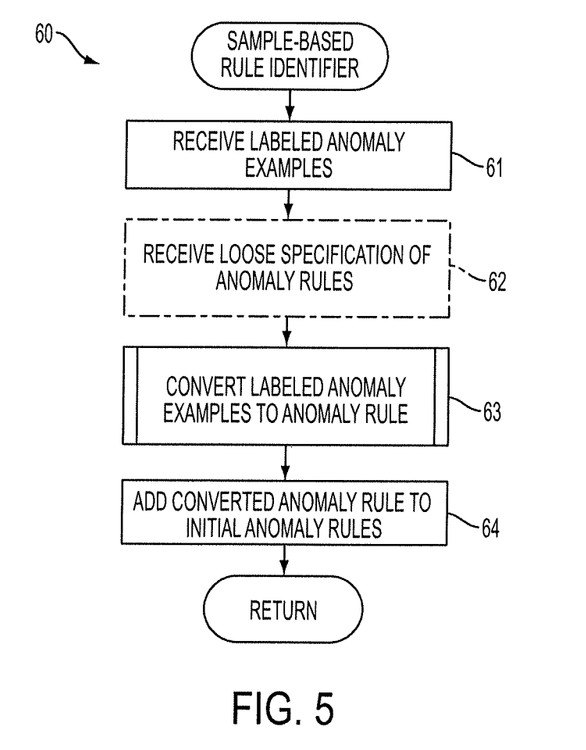
FIG. 5 is a flow diagram showing a routine for performing sample-based rule identification for a verified anomaly for use in the method of FIG. 2.

All the data points found to be anomalies through the statistical anomaly detection methods are further verified and labeled by domain experts. Domain experts are usually persons who possess specific knowledge in the data and thus are able to distinguish anomalies from a data set. Verification by the domain experts is critical in a process of anomaly detection for identifying false-positive and false-negative data points which are often mistakenly identified by the statistical analysis. Further, verification of domain experts can replace known and statistically detected anomalies to new forms of manipulative behavior which are more current of interest. In other words, new domain expertise can always be incorporated into the anomaly detection system by verification of domain experts. The domain experts verifies each suspected-anomaly based on the statistical analysis as normal or anomaly. The data which receives a label of normal by the domain experts is utilized to adjust algorithms for the statistical analysis, as further discussed infra with reference to FIG. 7. On the other hand, the data received a label of an anomaly by the domain experts is treated for further process. FIG. 5 is a flow diagram showing a routine 60 for performing sample-based rule identification for a verified anomaly for use in the method of FIG. 2. A sample-based rule identifier enables a simple feedback channel for using domain expertise and insights regarding the data set and increases an efficiency of anomaly detection by creating concrete and accurate anomaly rules. First, the labeled anomaly examples are received from the domain experts (step 61). If no single anomaly rule has yet been established, a loose specification of anomaly rules which is specified by the domain experts is also provided to the sample-based rule identification (step 62). The labeled anomaly examples are then converted into exact anomaly rules that contain a generalization of specific anomaly examples (step 63). The anomaly rule can be a group of anomaly rules. Other forms of anomaly rule are possible.

Figure 6A:
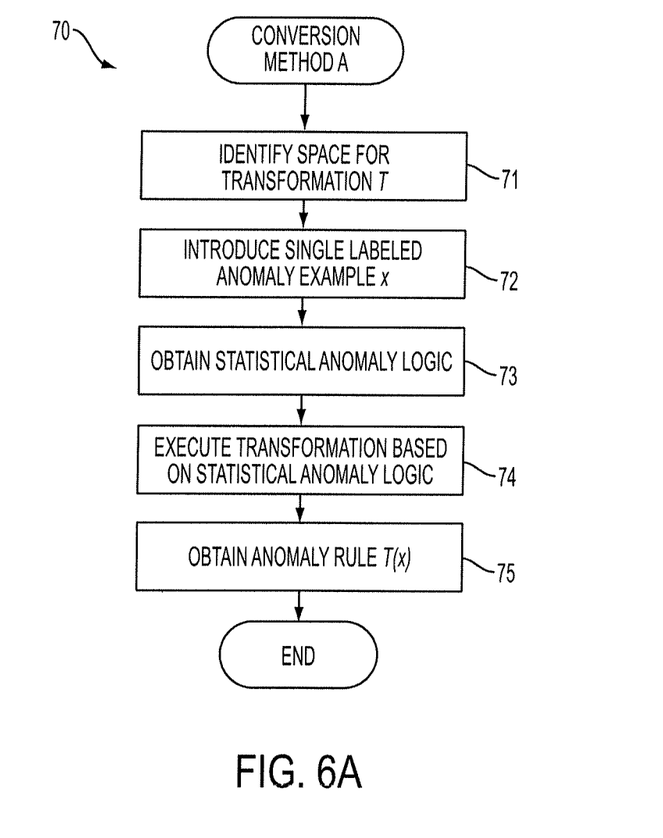
FIGS. 6a-c are flow diagrams showing routines for converting anomalies into anomaly rules for use in the method of FIG. 5.
Figure 6B:
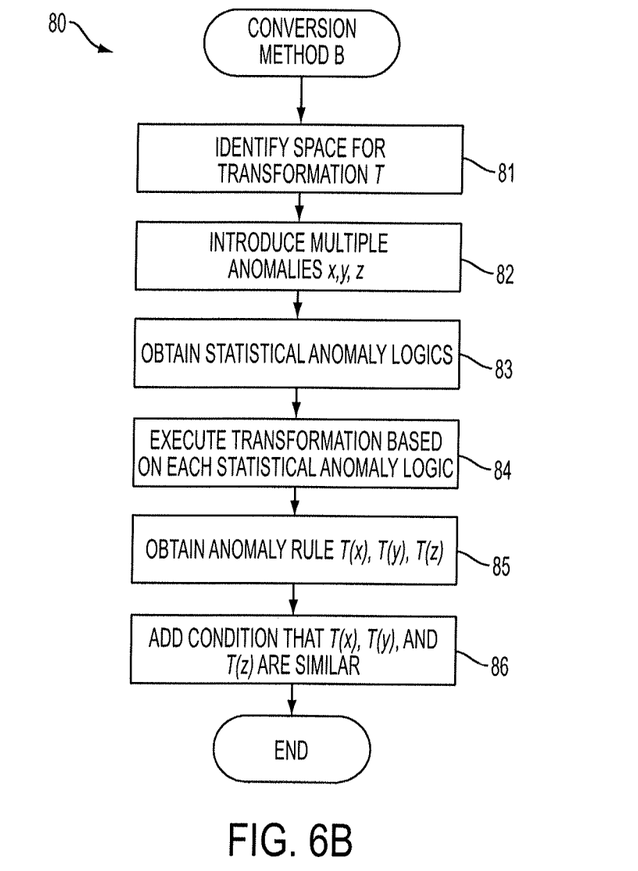
Figure 6C:
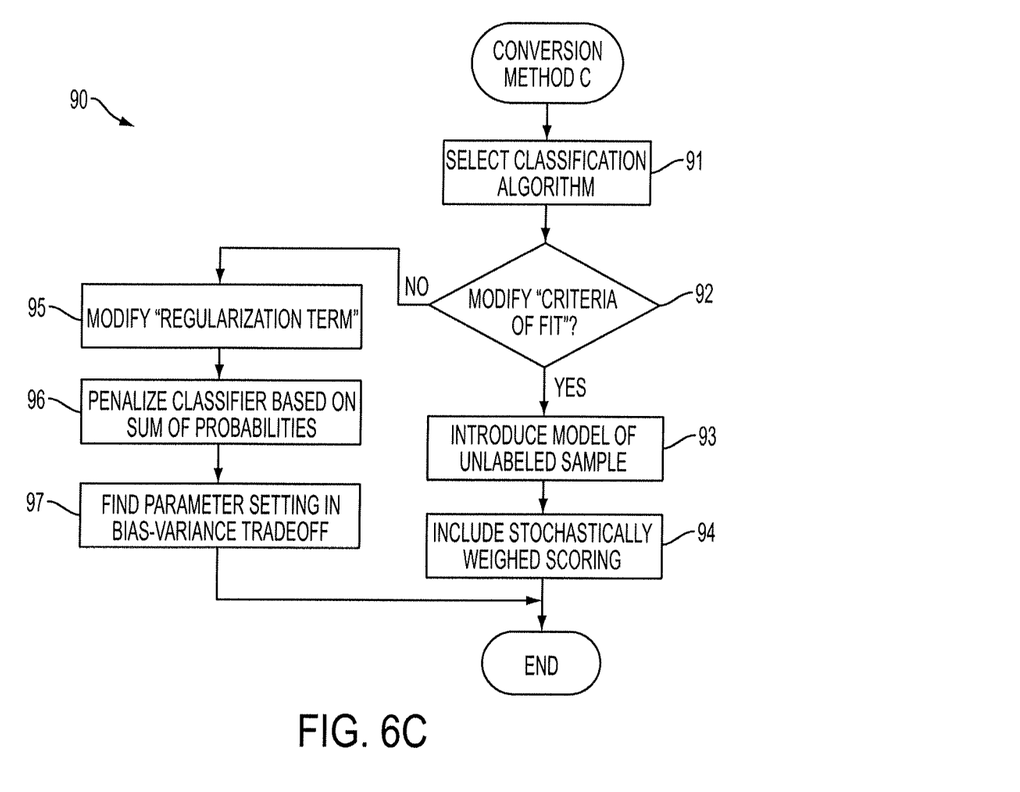

Conversion of anomaly examples into rules enables to incorporate domain expertise into the overall anomaly detection systems. By way of example, FIGS. 6a-c are flow diagrams showing routines 70, 80, 90 for converting anomalies into anomaly rules for use in the method of FIG. 5. FIG. 6a shows a simplest conversion method A for the labeled anomaly examples. First, a space for transformation T is identified (step 71). The transformation space T can be any function to map a set of data into another set of data. Then, a single labeled anomaly example x in a data set S is introduced (step 72). Logic and features of how the labeled anomaly example x is identified as anomaly is learned (step 73). This learning method can be supervised learning, unsupervised learning, or a combination of supervised and unsupervised learning. Other forms of learning methods are possible. Then, the transformation T for the data S, T(S) will be executed to identify anomalies based on the logic and features of the anomaly (step 74) and outputs an anomaly rule T(x) (step 75). As an example, a sample x in d-dimensional multivariate data S is identified as an anomaly by a distance-based statistical method as a ratio of the first dimension of x to the second dimension of x, $x[1]/x[2]$ is very large. The distance-based statistical method has been established, such as described in Chandola et al., Anomaly Detection: A Survey, *ACM Computing Surveys (CSUR)*, Vol. 41(3) Article No. 15, pp 25-30 (2009), the disclosures of which are incorporated herein by reference. The sample x identified as anomaly is further verified by a domain expert and determined to be a valid anomaly. The sample x is then fed to a sample-rule based identification method, which generalizes the sample x into a rule by using a transformation T and obtains an anomaly rule T(x) which is x[1]/x[2] to describe the space in which x is anomalous. For identifying other anomalies x1, . . . xn, the anomaly rule T(xj) identifies anomalies in data S. For this specific example x, a threshold p is set for identifying anomalies as x[1]/x[2]>p. This threshold p can be determined by using entropy-based measures that detect the change in uncertainty in T(S) with and without the anomalous points, as further discussed infra with reference to FIG. 7. Other threshold methods are possible. This conversion method A can be extended to multiple samples in an almost identical manner. Multiple samples can be used to explicitly convey specific dimensions of interest.

Conversion of multiple anomaly examples into an anomaly rule is also possible. FIG. 6*b* shows a conversion method B for multiple labeled anomaly examples. Similar to FIG. 6*a*, a space for transformation T is identified (step 81). Then, multiple labeled anomaly examples x, y, z in a data set S are introduced (step 82). Logic and features of how each labeled anomaly example x, y, z is identified as anomaly are learned (step 83). This learning method can be supervised learning, unsupervised learning, or a combination of supervised and unsupervised learning. Other forms of learning methods are possible. Then, the transformation T for the data S, T(S) will be executed to identify anomalies based on the logic and features of the anomalies x, y, z (step 84) and outputs anomaly rules T(x), T(y), T(z) (step 85). The transformation T must be conditioned that T(x), T(y), and T(z) are similar (step 86) as the transformation T is ensured to select the dimensions along which the samples x, y, and z are similar.

When there are multiple anomalous samples and unlabeled samples in a data set S, existing classification algorithms can be modified to classify anomalies. FIG. 6*c* shows a conversion method C for establishing an anomalous classifier. In general, many classification algorithms explicitly or implicitly optimize criteria of fit to training data. The criteria of fit can be maximum likelihood, squared errors, or other loss functions, such as margin from the classification. Further, many classification algorithms explicitly or implicitly include a regularization term. The regularization term can be a measure of complexity weighted by a smoothness parameter. Thus, modifying a classification algorithm can be focused on either the criteria of fit or the regularization term. First of all, a targeted classification algorithm is selected for conversion (step 91). If the criteria of fit is selected to modify (step 92), a model of unsupervised samples is introduced (step 93). In one embodiment, this model can include an a-priori model of probability that a sample is anomalous. In another embodiment, a model of how likely a sample will be discovered to be anomalous can be included into the model of unsupervised samples. For example, the model can assume that the age of a sample in a database is correlated with discovering that it is anomalous. In this example, older samples can be less likely to be anomalous. In another example, an earlier audit of a subset of samples might have increased the probability that those samples, if anomalous, would be labeled anomalous. In this example, the model can be structured based on the audit history. In further another embodiment, stochastically weighted scoring of the unlabeled samples can be used to modify the criteria of fit. For example, the unlabeled samples can be weighted as "normal." This approach is specifically beneficial when there is a well understood a-priori model for an anomalous label and a model of how anomalous labeling is discovered. Other forms of model can be used for the modification of criteria of fit.

In a situation where less is known about the anomalous label, modifying the model to another machine learning algorithm which regularization is similar to the model is useful. Such situations are when each sample is anomalous with unknown parameters, or although the structure of the model is known, such as the model includes an audited subset, the probability of discovery in the subset is unknown. By basing some formulation of the regularization of another model, parameters of another model and parameters of a classifier can be learned. Once the criteria of fit is not selected for modification, a regularization term can be modified (step 95). A regularization term which penalizes an anomaly rule or classifier according to some aggregate function, such as a sum, of the probabilities under a model that classify all points as suspicious (step 96). In this way, the classifier puts suspicious points in a suspicious class to match with anomaly labels provided by domain experts and excludes high-probability points in the population. In one embodiment, there are several hyper-parameters to control the algorithm so that the relative importance of constraints provided by the domain experts can be controlled and the rareness of examples classified as suspicious can be maximized. Once the formulation occurs, a parameter setting in a bias-variance tradeoff that minimized the prediction error in a test sample is found.

Figure 7:
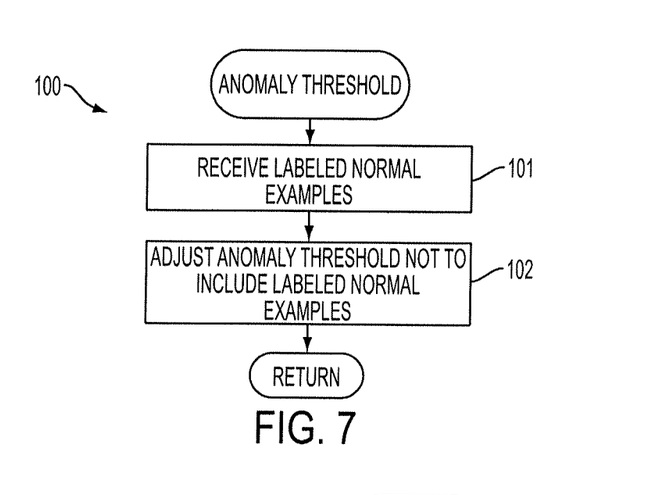
FIG. 7 is a flow diagram showing a routine for adjusting an anomaly threshold for use in the method of FIG. 2.

Verified normal examples in the data set are utilized for adjusting the statistical anomaly detection algorithms, especially for outlier identification based methods. FIG. 7 is a flow diagram showing a routine 100 for adjusting an anomaly threshold for use in the method of FIG. 2. Referring back to FIG. 3 as discussed supra, by way of example, risk scores for all the pharmacies for a particular violation type are identified in a histogram. The statistical anomaly detection algorithm used in this example identifies pharmacies whose scores do not fit within the trend of the histogram. The horizontal axis indicates various discrete score intervals for all the pharmacies and the horizontal axis indicates a score frequency. As discussed supra in FIG. 3, most of the pharmacies are found in two regions 41, 42. The scores in two regions 41, 42 follow a normal decay pattern and are considered to be normal that may not be engaged in fraud transactions. However, other three regions 43, 44, 45 indicate that a small number of pharmacies have anomalous scores within the intervals which do not fit within the normal decay pattern of the histogram. The statistical anomaly detection algorithm enables to identify regions 43, 44, 45 and determine them as anomalies. If a sample x in the region 43 is mistakenly identified by the statistical anomaly detection algorithm as anomalous but later verified by the domain experts as normal (step 101), a threshold between 43 and 44 can be applied to the statistical anomaly detection algorithm to supply additional verification so that the statistical anomaly detection algorithm will not mistakenly identify normal examples such as 43 (step 102).

For setting the threshold, an entropy based method can be used. Based on the entropy based method, if anomalies exist in a dataset S of scores, empirical distribution corresponding to the data set S will be dispersed due to the additional mode corresponding to the anomalies and as a result, the corresponding entropy E will be high. On the other hand, if the dataset S contains no anomalies, the scores in the dataset is more concentrated and the entropy of the dataset S will be correspondingly similar. Therefore, when transitioning one region in the dataset S which does not contain anomalies to another region in the dataset S which contains anomalies, there will be a sharp decrease in entropy. An entropy E for each region is calculated as $E=\Sigma_{i \in s}P(vi) \times (\log P(vi))$ and for each element i, a surprise ratio $s_i$ is calculated as $$si = \frac{-\log p(vi)}{E}.$$

The surprise ratio $s_i$ is a measure of how consistent or random a given sample point $s_i$ is with regard to the rest of the data set. In one embodiment, when the surprise ratio at sample point $s_i$ is large, the sample point $s_i$ is considered to be anomaly. Other methods for setting thresholds are possible.

Figure 8:
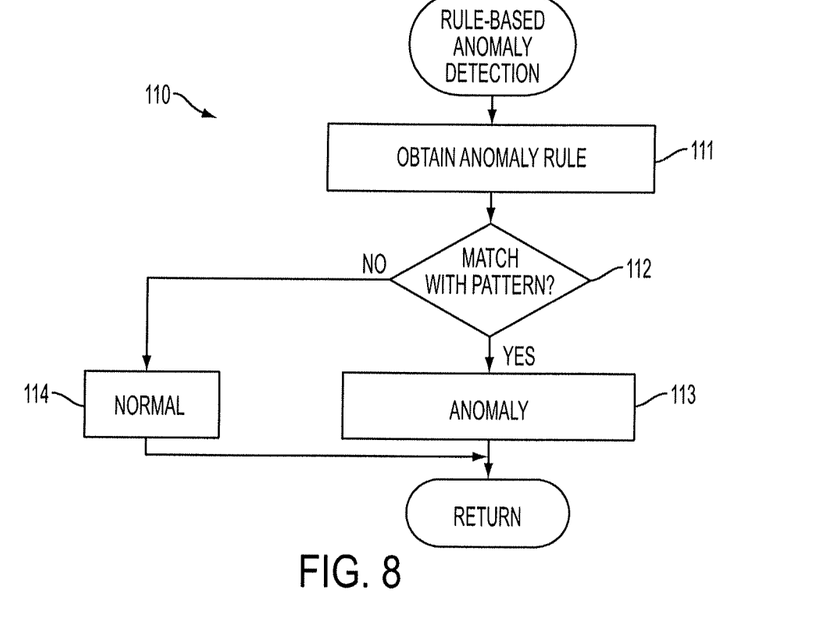
FIG. 8 is a flow diagram showing a routine for discovering anomalies based on a rule-based anomaly detection for use in the method of FIG. 2.

Once the anomaly rule is generated or adjusted based on the verified anomaly examples and domain expert-chosen concrete rules, a rule-based anomaly detection is performed to identify further anomalies in the dataset. A rule-based anomaly detection method can be used to detect specific instances of known forms of manipulative behavior. FIG. 8 is a flow diagram showing a routine 110 for discovering anomalies based on a rule-based anomaly detection for use in the method of FIG. 2. By way of example, a pattern recognition method can be used as a rule-based anomaly detection method. Other rule-based anomaly detection methods are possible. The anomaly rule is obtained from the sample-based rule identification or concrete specification by domain experts (step 111). A pattern identified in the anomaly rule is then matched with each data point in the data set (step 112). If a data point matches with the identified anomaly pattern, then the data point will be labeled as anomaly (step 113). On the other hand, if the data point does not match with the identified anomaly pattern, then the data point is labeled as normal and will be discarded. In this way, an accurate and domain expertise-incorporated anomaly detection is performed to identify anomalies from the data set. Other forms of the rule-based anomaly detection method are possible.

While the invention has been particularly shown and described as referenced to the embodiments thereof, those skilled in the art will understand that the foregoing and other changes in form and detail may be made therein without departing from the spirit and scope of the invention.

What is claimed is:

1. A system for detecting anomalies using sample-based rule identification with the aid of a digital computer, comprising:
  a non-transitory computer readable storage medium comprising program code and further comprising:
    a database comprising a data set for data analytics, the data set comprising a plurality of data points; and
    a set of anomaly rules;
  a computer processor and memory with the computer processor coupled to the storage medium, wherein the computer processor is configured to execute the program code to perform steps to:
    statistically identify one or more of the data points in the data set comprised in the database as one or more potential anomalies, comprising calculating a statistics for each of the data points;
    label each of the identified data points as at least one of anomaly and non-anomaly based on verification by a domain expert;
    adjust the set of anomaly rules comprised in the database based on at least one of the labeled anomalies, comprising creating an additional anomaly rule and adding the rule to the set, further comprising:
      determine an entropy of at least a portion of a different data set, the different data set comprising the statistics of all of the data points, the at least the portion comprising the statistics for the at least one anomaly;
      use the entropy to set a threshold; and
      set the additional anomaly rule to label one or more of the data points other than the at least one labeled anomaly as one or more additional anomalies upon the statistics for these data points exceeding the threshold;
    detect and classify as the one or more additional anomalies the one or more data points other than the at least one labeled anomaly comprised in the database by applying the adjusted set of anomaly rues comprised in the database to the statistics for the data points; and
    control manipulative malicious activities in at least one of the fields of social welfare, credit card, transportation systems, the Internet networks, and healthcare systems based on the labeled anomalies and the additional anomalies.

2. A system according to claim 1, wherein the computer processor is further configured to execute the program code to perform steps to:
  recognize one of the identified data points as the labeled non-anomaly; and
  modify the set of anomaly rules based on the recognition.

3. A system according to claim 1, wherein the set of the rules are adjusted based on a plurality of the anomalies, and the statistics comprises a ratio along at least two dimensions.

4. A system according to claim 1, wherein the computer processor is further configured to execute the program code to perform steps to:
  select a classification algorithm; and
  modify the classification algorithm wherein the computer processor is further configured to execute the program code to perform steps to at least one of:
    modify criteria of fit; and
    modify a regularization term.

5. A system according to claim 1, further comprising:
  the non-transitory computer readable storage medium further comprising:
    an anomaly threshold comprised in the set of anomaly rules; and
    a score of the labeled non-anomaly;
  wherein the computer processor is further configured to execute the program code to perform steps to:
    refine the set of anomaly rules by comparing the score of the labeled non-anomaly to the anomaly threshold and raising the anomaly threshold if the score of the labeled non-anomaly is below the anomaly threshold.

6. A system according to claim 1, wherein the computer processor is further configured to execute the program code to perform steps to at least one of:
  statistically detect incidents in the data set comprised in the database that occur less frequently than the rest of the population in the data set comprised in the database;
  statistically detect trends in the data set comprised in the database with regard to time; and
  statistically detect a correlation between one or more events in the data set comprised in the database.

7. A method for detecting anomalies using sample-based rule identification with the aid of a digital computer, comprising the steps of:
- maintaining a data set for data analytics comprised in a storage medium, the data set comprising a plurality of data points;
- statistically identifying with a computer processor and memory with the computer processor coupled to the non-transitory computer readable storage medium one or more of the data points in the data set comprised in the database as one or more potential anomalies, comprising calculating a statistics for each of the data points;
- labeling each of the identified data points with the computer processor as at least one of anomaly and non-anomaly based on verification by a domain expert;
- defining a set of anomaly rules comprised in the storage medium based on at least one of the labeled anomalies, comprising creating one of the anomaly rules and adding the rue to the set, further comprising:
  - determining an entropy of at least a portion of a different data set, the different data set comprising the statistics of all of the data points, the at least the portion comprising the statistics for the at least one anomaly;
  - using the entropy to set a threshold; and
  - setting the additional anomaly rule to label one or more of the data points other than the at least one labeled anomaly as one or more additional anomalies upon the statistics for these data points exceeding the threshold;
- detecting and classifying as the one or more additional anomalies the one or more data points other than the at least one labeled anomaly in the data comprised in the database with the computer processor by applying the set of anomaly rules to the statistics for the data points; and
- controlling manipulative malicious activities in at least one of the fields of social welfare, credit card, transportation systems, the Internet networks, and healthcare systems based on the labeled anomalies and the additional anomalies.

8. A method for detecting anomalies using sample-based rule identification with the aid of a digital computer, comprising the steps of:
- maintaining a data set for data analytics in a database comprised in a non-transitory computer readable storage medium, the data set comprising a plurality of data points;
- defining a set of anomaly rules comprised in the database comprised in the storage medium;
- statistically identifying with a computer processor and memory with the computer processor coupled to the non-transitory computer readable storage medium one or more of the data points in the data set comprised in the database as one or more potential anomalies, comprising calculating a statistics for each of the data points;
- labeling the identified data points with the computer processor as at least one of anomaly and non-anomaly based on verification by a domain expert;
- adjusting the set of anomaly rules comprised in the database with the computer processor based on the labeled anomalies, comprising creating an additional anomaly rule and adding the additional rule to the set, further comprising:
  - determining an entropy of at least a portion of a different data set the different data set comprising the statistics of all of the data points, the at least the portion comprising the statistics for the at least one anomaly;
  - using the entropy to set a threshold; and
  - setting the additional anomaly rule to label one or more of the data points other than the at least one labeled anomaly as one or more additional anomalies upon the statistics for these data points exceeding the threshold;
- detecting and classifying as the one or more additional anomalies the data points other than the at least one labeled anomaly comprised in the database with the computer processor by applying the adjusted set of anomaly rules comprised in the database to the data set statistics for the data points; and
- controlling manipulative malicious activities in at least one of the fields of social welfare, credit card, transportation systems, the Internet networks, and healthcare systems based on the labeled anomalies and the additional anomalies.

9. A method according to claim 8, further comprising:
- recognizing one of the identified data points with the computer processor as the labeled non-anomaly; and
- modifying the set of anomaly rules with the computer processor based on the recognition.

10. A method according to claim 8, wherein the set of the rules are adjusted based on a plurality of the anomalies, and the statistics comprises a ratio along at least two dimensions.

11. A method according to claim 8, further comprising:
- selecting with the computer processor a classification algorithm; and
- modifying the classification algorithm with the computer processor comprising at least one of:
  - modifying with the computer processor criteria of fit; and
  - modifying with the computer processor a regularization term.

12. A method according to claim 8, further comprising:
- defining an anomaly threshold with the computer processor comprised in the set of anomaly rules;
- defining with the computer processor a score of the labeled non-anomaly; and
- refining the set of anomaly rules with the computer processor by comparing the score of the labeled non-anomaly to the anomaly threshold with the computer processor and raising the anomaly threshold with the computer processor if the score of the labeled non-anomaly is below the anomaly threshold.

13. A method according to claim 8, further comprising at least one of:
- statistically detecting incidents in the data set comprised in the database with the computer processor that occur less frequently than the rest of the population in the data comprised in the database;
- statistically detecting trends in the data set comprised in the database with the computer processor with regard to time; and
- statistically detecting a correlation between one or more events in the data set comprised in the database.

* * * * *